(12) United States Patent
Dijkhuizen Borgart et al.

(10) Patent No.: US 8,809,054 B2
(45) Date of Patent: Aug. 19, 2014

(54) CELL-CULTURE-BAG

(75) Inventors: Elise Leonore Isolde Dijkhuizen Borgart, Nieuwegein (NL); Madelon Sophia George Maria Bracke, Zeist (NL); Joost Dick De Bruijn, Amersfoort (NL)

(73) Assignee: Xpand Biotechnology B.V., Bilthoven (NL)

( * ) Notice: Subject to any disclaimer, the term of this patent is extended or adjusted under 35 U.S.C. 154(b) by 0 days.

(21) Appl. No.: 13/697,346

(22) PCT Filed: May 11, 2011

(86) PCT No.: PCT/NL2011/050318
§ 371 (c)(1),
(2), (4) Date: Nov. 9, 2012

(87) PCT Pub. No.: WO2011/142667
PCT Pub. Date: Nov. 17, 2011

(65) Prior Publication Data
US 2013/0059383 A1    Mar. 7, 2013

(30) Foreign Application Priority Data

May 12, 2010   (EP) .................................... 10162688

(51) Int. Cl.
*C12N 5/071*   (2010.01)
*C12N 5/00*    (2006.01)

(52) U.S. Cl.
CPC ............ *C12N 5/0075* (2013.01); *C12N 5/0663* (2013.01)
USPC ....................................................... 435/403

(58) Field of Classification Search
CPC ........................... C12N 5/0075; C12N 5/0663
See application file for complete search history.

(56) References Cited

U.S. PATENT DOCUMENTS

| | | | |
|---|---|---|---|
| 6,190,913 B1 | 2/2001 | Singh | |
| 6,544,788 B2 | 4/2003 | Singh | |
| 7,456,019 B2 * | 11/2008 | Goodwin et al. | 435/394 |
| 7,709,251 B2 * | 5/2010 | Ellis et al. | 435/305.1 |
| 2003/0036192 A1 | 2/2003 | Singh | |
| 2005/0244963 A1 | 11/2005 | Teplyashin | |
| 2007/0264713 A1 | 11/2007 | Terstegge et al. | |
| 2009/0130704 A1 | 5/2009 | Gyure | |
| 2010/0075406 A1 | 3/2010 | Tanaka et al. | |
| 2011/0070648 A1 * | 3/2011 | Anneren et al. | 435/380 |

FOREIGN PATENT DOCUMENTS

| | | |
|---|---|---|
| JP | 2009291097 | 12/2009 |
| WO | WO-2008/060037 | 5/2008 |
| WO | WO-2009/139703 | 11/2009 |
| WO | WO-2011/142670 | 11/2011 |

OTHER PUBLICATIONS

Singh, "Disposable bioreactor for cell culture using wave induced agitation", Cytotechnology, 30;149-158, 1999.*
Nagel et al. (1992) "Glossary for Chemists of Terms Used in Biotechnology (IUPAC Recommendations 1992)," Pure & Appl. Chem. 64(1):143-168.
Schop et al. (2008) "Expansion of Mesenchymal Stem Cells Using a Microcarrier-Based Cultivation System: Growth and Metabolism," Journal of Tissue Engineering and Regenerative Medicine 2:126-135.
International Preliminary Report on Patentability issued for International Patent Application No. PCT/NL2011/050322, dated Nov. 13, 2012, 7 pages.
Bing et al., "The Use of Microcarrier Beads in the Production of Endothelium-Derived Relaxing Factor by Freshly Harvested Endothelial Cells," Tissue and Cell (1991) 23(2):151-159.
Hung et al., "Isolation and Characterization of Size-Sieved Stem Cells from Human Bone Marrow," Stem Cells (2002) 20:249-258.
International Search Report for PCT/NL2011/050318, Jul. 28, 2011, 3 pages.
Oh et al., "Long-term microcarrier suspension cultures of human embryonic stem cells," Stem Cell Research (2009) 2:219-230.
Schop et al., "Expansion of human mesenchymal stromal cells on microcarriers: growth and metabolism," Journal of Tissue Engineering and Regenerative Medicine (2010) 4:131-140.

* cited by examiner

*Primary Examiner* — Ruth Davis
(74) *Attorney, Agent, or Firm* — Morrison & Foerster LLP

(57) ABSTRACT

The present invention is directed to a method to expand adherent cells comprising addition of adherent cells to an expansion container comprising microcarriers and culture medium; removing medium from the expansion container through a 8-20 mm filter; allowing cells to attach to microcarriers and keeping the expansion container in motion with an angle of between 30 to 90° and −30 to −90°. The present invention is also directed to a device suitable in the method. The advantage of the present invention is that fewer steps are needed to expand adherent cells, including stem cells like MSC opening the way for the use of autologeous and allogenous stem cell therapy. In addition, contamination risk is limited since the present invention may be carried out in a closed, disposable system.

18 Claims, 2 Drawing Sheets

CELL-CULTURE-BAG

CROSS-REFERENCE TO RELATED APPLICATIONS

This application is the national phase of PCT application PCT/NL2001/050318 having an International filing date of 11 May 2011, which claims benefit of European patent application No. 10162688.5 filed 12 May 2010. The contents of the above patent applications are incorporated By reference herein in their entirety.

The present invention relates to expansion of adherent cells, more importantly of stem and progenitor cells.

BACKGROUND

The generation of replacement tissue in cell culture, commonly known as "tissue engineering", the provision of surrogate cells for cell-based transplantation therapies, and the identification of new drugs using cell based high-throughput methods all represent important examples of innovative biotechnology-based applications. Stem cells in particular represent an important source for implementing such biotechnological applications because stem cells, in contrast to primary cells, can readily serve as a potentially unlimited source for obtaining differentiated, specific cell types. However, the cultivation of undifferentiated stem cells has proven to be very complex and furthermore, particularly sensitive to external influences.

Aseptic bioreactors require cleaning, sterilization and validation of the standard stainless steel or glass bioreactors by the customer. The use of presterilized disposables that need not be cleaned, sterilized or validated by end users provides savings of costs and multiple hours of labor per run. Furthermore, plastics are lightweight, easy to transport, and require less room than stainless steel or glass vessels. Wave Biotech (Bridgewater, N.J.) has developed a range of presterile, disposable bioreactors that do not require cleaning or sterilizing by the end user. The Wave Bioreactor is made of sheets of flexible, gas impermeable material. The bag is partially filled with media and then inflated with air that continually passes through the bag's headspace. The media is mixed and aerated by rocking the bags up to 40 times a minute to increase the air-liquid interface. However, since a solid housing does not support the bags, the bags become unwieldy and difficult to handle as they increase in size. Furthermore, the wave action within the rocking bag due to the air in the headspace creates damaging turbulent forces. Certain cell cultures, particularly human cell cultures, thrive better under more gentle conditions.

Stem cells may be used for regeneration of heart muscle tissue after a heart infarction and also in vascular regeneration in chronic heart diseases. Furthermore the formation of bone and cartilage from stem cells is well known. Therapeutic applications of stem cells are most beneficial if the stem cells are autologous, i.e. from the person him/herself. The advantages of using autologous cells are evident, cells will always match and rejection of the cells will not happen, so strong immunosuppressive drugs are not necessary as with allografts. In addition, infection risks with hepatitis and HIV are reduced and allergic reactions are diminished. However also allogenous cells may be used, e.g. when no healthy stem cells can be extracted from the patient.

Some cells are adherent, such as mesenchymal stem cells (MSC) and grow only on a surface. These adherent cells can be grown in tissue culture flasks where the cells attach to the plastic surface. It has been shown that they may also be grown on microcarriers (Schop et al, J Tissue Eng Regen Med 2008; vol 2 pages 126-135). WO2009/139703 discloses a method for cell expansion, such as MSC on microcarriers in a plastic bag reactor. The method however uses purified patient tissue, wherein the cells of interest are isolated. The isolated cells are pre-cultured in a T-flask to achieve enough MSC before they are applied to the microcarriers in the plastic bag reactor. This preculture step entails several drawbacks. Additional material is needed, i.e. the T-flask, giving more costs. Furthermore, the cells are first isolated and cultured in the T-flask, meaning additional steps and thus more involvement of highly trained, and thus expensive, persons are needed. In addition, the preseeded cells need to be collected and transferred to the plastic bag, which increases the risk of contamination due to the transfer step.

Up to now there is no cell expansion method available that is capable of using crude patient cell samples without needing to purify, isolate and pre-culture the cells before using a disposable bioreactor to expand the cells.

It is therefore an object of the present invention to have a cell expansion method that is capable of using cell and tissue samples that contains more than the cells of interest. The present invention has the advantage that cells of interest need not be isolated from biopsies of patients. The biopsies that still have the cellular composition of the tissue in the patients may be used without laborious isolation and purification steps.

The present invention provides a solution by using microcarriers in combination with a small pore filter and a specific rocking regime of the bioreactor.

DETAILED DESCRIPTION

Definitions

Stem cells: the classical definition of a stem cell requires that it possess two properties: Self-renewal—the ability to go through numerous cycles of cell division while maintaining the undifferentiated state. Potency—the capacity to differentiate into specialized cell types. In the strictest sense, this requires stem cells to be either totipotent, pluripotent or multipotent—to be able to give rise to any mature cell type, although unipotent stem cells have also been described.

The two broad types of mammalian stem cells are: embryonic stem cells that are isolated from the inner cell mass of blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues.

Totipotent (a.k.a omnipotent) stem cells can differentiate into embryonic and extraembryonic cell types. Such cells can construct a complete, viable, organism. These cells are produced from the fusion of an egg and sperm cell. Cells produced by the first few divisions of the fertilized egg are also totipotent.

Pluripotent stem cells are the descendants of totipotent cells and can differentiate into nearly all cells i.e. cells derived from any of the three germ layers.

Multipotent stem cells can differentiate into a number of cells, but only those of a closely related family of cells, usually within the germ layer that the mesenchymal stem cell originates from.

Unipotent cells can produce only one cell type, their own, but have the property of self-renewal which distinguishes them from non-stem cells (e.g. skin stem cells).

Adult stem cells refer to any cell which is found in a developed organism that has two properties: the ability to divide and create another cell like itself and also divide and create a cell more differentiated than itself. Adult stem cells can be found in children, as well as adults. Pluripotent adult stem cells are rare and generally small in number but can be found in a number of tissues including umbilical cord blood and bone marrow. Most adult stem cells are lineage-restricted (multipotent) and are generally referred to by their germ-layer or tissue origin (mesenchymal stem cell, adipose-derived stem cell, endothelial stem cell, etc.). Adult stem cell treatments have been successfully used for many years to treat leukemia and related bone/blood cancers through bone marrow transplants. Adult stem cells are also used in veterinary medicine to treat tendon and ligament injuries in horses. Adult stem cells can be obtained from the intended recipient, (an autograft) the risk of rejection is essentially non-existent in these situations.

Hematopoietic stem cells (HSCs) are non-adherent multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). Hematopoietic stem cells are found in the bone marrow of adults. Cells can be obtained directly by removal from the hip using a needle and syringe, or from the blood following pre-treatment with cytokines, such as G-CSF (granulocyte colony-stimulating factors), that induce cells to be released from the bone marrow compartment. Other sources for clinical and scientific use include umbilical cord blood, placenta, mobilized peripheral blood. For experimental purposes, fetal liver, fetal spleen, and AGM (Aorta-gonad-mesonephros) of animals are also useful sources of HSCs.

Mesenchymal stem cells (MSCs) are of stromal origin and may differentiate into a variety of tissues. MSCs have been isolated from placenta, adipose tissue, lung, bone marrow and blood, Wharton's jelly from the umbilical cord, and teeth (perivascular niche of dental pulp and periodontal ligament). Cell types that MSCs have been shown to differentiate into in vitro or in vivo include osteoblasts, chondrocytes and adipocytes. MSC are sometimes referred to Marrow Stromal Cell or Mesenchymal Stromal Cell and have been used interchangeably.

Microcarriers

Microcarriers (or "carriers") of the present invention include support materials for cultivating adherent growing cells. Microcarriers are defined in the IUPAC Compendium of Chemical Terminology (2nd Edition, 1992, Vol. 64, p. 160). A microcarrier can be defined as a microscopic bead or sphere that increases the surface area in a tissue culture for the attachment and yield of anchorage-dependent cells.

Microcarriers of the present invention are carrier materials, preferably spherical in form and suitable for cultivating adherent growing cells, in particular animal cells, in suspension. Microcarriers may be produced from a wide variety of materials, including plastic, glass, ceramic, silicone, gelatin, dextran, cellulose and others. In addition, microcarriers can be pretreated in various ways including plasma treatment of the plastic surfaces that results in creating a hydrophilic surface, or the carriers can be coated (e.g. with gelatin, fibronectin, laminin, polyomithine, matrigel, or with binding motifs of the RGD binding domain of fibronectin). Suitable commercially available microcarriers include Cytodex 1, Cytodex 3, Cytopore (Amersham Biosciences), Cultispher G, Cultispher S (Perbio), Pronectin, FACT (Sigma), Biosilon, Microhex 2D (Nunc), and ImmobaSil (Dunn).

Medium as used in the present invention refers to a growth medium or culture medium which is a liquid or gel designed to support the growth of desired cells. There are different types of media for growing different types of cells, and contains all the nutrients required for cell growth.

Perfusion is the process of nutritive delivery of medium to a cell culture. The perfusion system may deliver the medium continuously over time but also in batch on demand, e.g. when monitoring cell viability. The perfusion may be manual or via a pump. A preferred perfusion system may be automated e.g. wherein the cell viability is determined automatically and the nutrients needed are provided automatically.

A biopsy is a sample of cells or tissue removed from a living being. A biopsy may be an entire lump or area that is removed, (excisional biopsy). When a sample of tissue or fluid is removed with a needle in such a way that cells are removed without preserving the histological architecture of the tissue cells, the procedure is called a needle aspiration biopsy, or aspirate. In the present invention, the word biopsy and aspirate are used interchangeably. A biopsy or aspirate may be of any size, depending on the amount of cells needed and the amount of cells a living being may be able to donate.

Biopsies and aspirates may be further purified or modified, e.g. a filter step or gradient purification to remove certain ingredients of the biopsy or aspirate, e.g. certain cells or proteins. In some cases additional tissue other than the desired biopsy tissue is present in the biopsy or aspirate due to the technique of extracting the biopsy. For example when obtaining a bone marrow biopsy one has to go through the skin and possible a fat layer and then through the bone tissue in order to reach the bone marrow. The bone marrow biopsy then may contain bone chips and lumps of fatty tissue or cell aggregates. The additional tissue is often removed from the biopsy; however the cellular composition of the biopsy is still the same as the tissue in the living being from which it is withdrawn. Biopsies wherein only the additional tissue is removed and the cellular composition of the biopsy is the same as the cellular composition of the living tissue are referred to as cellular or crude biopsies. For example in the case of bone marrow aspirate, the bone chips, fatty tissue or cell aggregates are removed by a course filter to make sure that the cellular composition of the aspirate is the same as the bone marrow in the living being it was extracted from. This is called a cellular or crude bone marrow aspirate. A cellular or crude bone marrow aspirate contains a mixture of cells (e.g. red blood cells, platelets, white blood cells, fat cells and Mesenchymal stem cell) which is comparable to the bone marrow as it is present in the organism. Often in the prior art expansion methods for stem cells, the stem cells are purified from the biopsy so that a fraction is obtained where mainly the desired (stem) cells are present and the other cells present in a biopsy, such as e.g red blood cells, platelets, are removed. To indicate the difference of the present invention to the prior art expansion methods, (cellular) crude biopsies can be used in the present invention while for many of the prior art expansion methods, the (cellular) crude biopsy needs to be further purified prior to expansion to purify the desired cells first.

Figure 1:
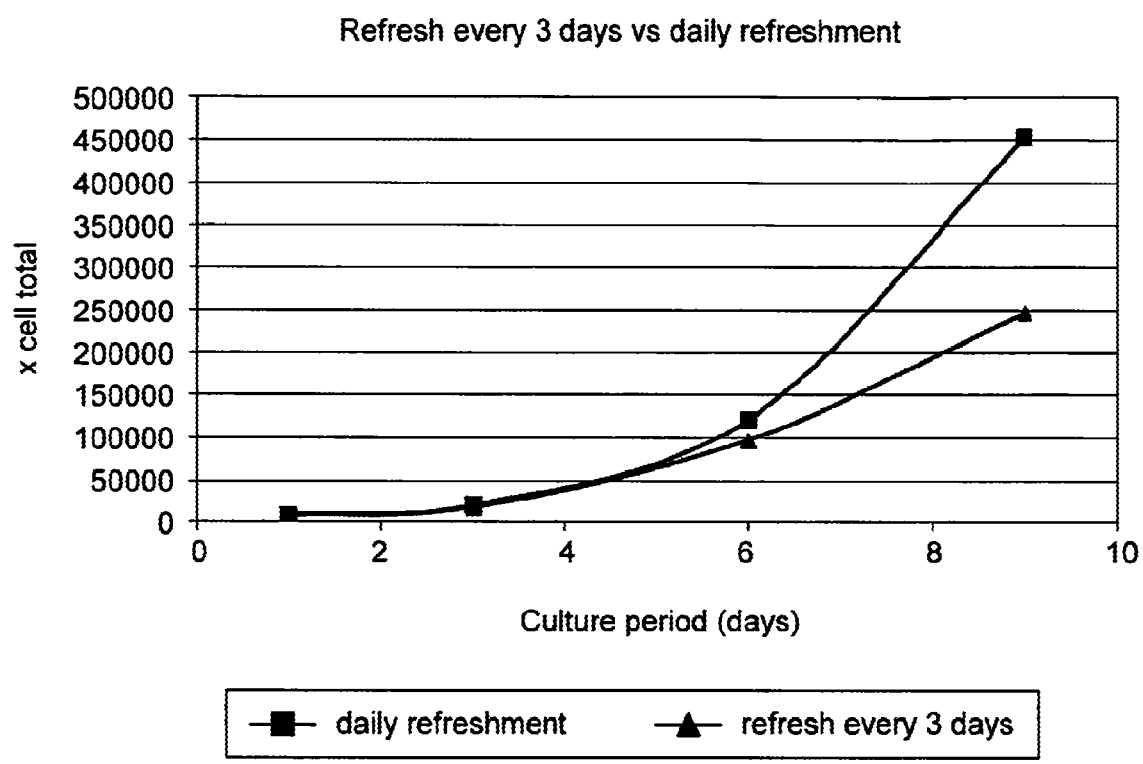
FIG. 1: Growth curves for daily refreshment compared to refreshment every 3 days

In a preferred embodiment, the expansion container is kept in motion with an angle of between 30 to 90° and −30 to −90° or with a rotating motion. The cells attached to the microcarriers grow optimal when the microcarriers are kept in a homogeneous suspension and are not allowed to settle or sediment. The force to keep the microcarriers in suspension should be such that the microcarriers are not allowed to settle or sediment however, the force should not be too much so to damage the cells. The movement of the microcarriers is carried out by rocking the expansion container. The rocking movement is at least between 30° and −30° when starting from a horizontal position (0°), more preferably between 50° to 90° and −50 to −90°, and most preferably between 60° to 80° and −60 to −80°. The rocking movement may go further than 90° and −90° (e.g. rotating), however that creates the same movement as going back from 90° or −90° to the horizontal position (0°). It is to be understood that rotating is comparable to a rocking movement between 90° to −90° from the horizontal position and is therefore included in the present invention. The speed of the rocking depends on the expansion volume; smaller expansion volumes require a relatively low rocking speed, whereas larger expansion volumes require a higher rocking speed. For expansion volume between 50 and 200 ml, a rocking speed of between 2 and 10 rpm is suitable, more suitable a rocking speed of between 3 and 8, most suitable between 4 and 6 rpm. In addition, there may be a stop time between and including the maximum/minimum rock angle, i.e. before the expansion container will return. A rocking speed between 1 and 50 rpm, or between 15 and 35 rpm, or even between 20 and 30 rpm is also suitable for expansion volume between 50 and 200 ml. In addition, there may be a stop time between and including the maximum/minimum rock angle, i.e. before the expansion container will return. For expansion volume between 100 and 1000 ml 10 to 20 rpm is suitable, more suitable between 12 and 16 rpm, and most suitable between 13 and 15 rpm. In addition, there may be a stop time between and including the maximum/minimum rock angle, i.e. before the expansion container will return. A rocking speed between 1 and 100 rpm or between 5 and 50 rpm, and even between 7 and 35 rpm is also suitable for an expansion volume between 100 and 1000 ml. The time the expansion container remains at the maximum/minimum rocking angle depends on the settlement time, i.e. it preferably allows the microcarriers to travel to the lowest point, however, the stop time is preferably not be too long for the microcarriers with the cells attached to stick together and form aggregates. The rocking angle, rocking speed and stop time depends on the sedimentation velocity and may be calculated with the Stokes sedimentation equation, which is well within the skills of a skilled person. A skilled person therefore knows how to optimize these parameters. When the volume is small, e.g. during the seeding phase a relatively slow rocking rate is needed to allow cell attachment. Preferred rocking rates are 1-20°/second, more preferably 5-15°/second, most preferably 7-12°/second. A rocking rate between 1-250°/second or between 20 and 150°/second, and even between 50 and 100°/second is also suitable during the seeding phase. When the culturing volume is larger, e.g. during the expansion phase a higher rocking rate is needed to prevent formation of microcarrier/cell aggregates and to maintain a homogeneous suspension. Preferred rocking rates are 1-30°/second, more preferred 5-20°/second, and most preferred 10-15°/second. A rocking rate between 1-300°/second or between 25 and 250°/second, and even between 50 and 150°/second is also suitable during the expansion phase. During the harvesting phase a relatively high rocking rate is needed to detach the adherent cells from the microcarriers. Preferred rocking rates are 5-45°/second, more preferred 10-30°/second, and most preferred 15-20°/second. A rocking rate between 1-350°/second, or between 50 and 250°/second, and even between 100 and 200°/second is also suitable during the harvesting phase.

The acceleration and deceleration represent a part of the rest time which allows to microcarriers to sediment through the container. During the process, the amount of adherent cells per microcarrier will increase. Therefore the microcarrier weight will increase and consequently the sedimentation speed will increase. Therefore, the acceleration and deceleration will vary through the process. When the volume is small, e.g. during the seeding phase a preferred acceleration/deceleration varies between $10\text{-}100°/s^2$, more preferred between $20\text{-}70°/s^2$, most preferred between $35\text{-}50°/s^2$. An acceleration/deceleration between $1\text{-}500°/s^2$, or between 150 and $400°/s^2$ and also between 200 and $300°/s^2$ is also suitable during the seeding phase. When the culturing volume is larger, e.g. during the expansion phase a preferred acceleration/deceleration varies between $10\text{-}150°/s^2$, more preferred between $20\text{-}100°/s^2$, most preferred between $40\text{-}60°/s^2$. An acceleration/deceleration between $1\text{-}700°/s^2$ or between 200 and $600°/s^2$, and even between 300 and $500°/s^2$ is also suitable during the expansion phase. During the harvesting phase a preferred acceleration/deceleration varies between 10-100°/s$^2$, more preferred between 20-70°/s$^2$, most preferred between 35-50°/s$^2$. An acceleration/deceleration between 1-990°/s$^2$ or between 200 and 800°/s$^2$ or even between 300 and 600°/s$^2$ and also between 400 and 500°/s$^2$ is also suitable during the harvesting phase.

In a preferred embodiment the adherent cells are present in a crude or cellular biopsy. In the present invention crude or cellular biopsy means a biopsy that has the same composition of cells as it has in the organism. The advantage of the present invention is that such a crude biopsy may be used without need of isolating desired cells. For example a crude bone marrow biopsy, where only the large bone chips and fat tissue is removed but has otherwise the same cellular make up as bone marrow in the organism may be used directly in the inventive method. No other treatment is necessary. No pre-washing or pre-culturing step is needed for the method of the present invention.

In a preferred embodiment the expansion container is disposable. Suitable disposable containers are so-called culture bag containers. The expansion chamber is preferably a bag type of container. In a preferred embodiment, the expansion chamber is made of flexible material. In a most preferred embodiment the expansion chamber is a disposable bag type container made of flexible material. Suitable disposable material is able to be sterilized. The advantage of having a disposable expansion container is that the expansion container is used only for one person, so that cross-contamination does not occur. It also obviates the need for extensive cleaning between two expansion runs. Preferred material may be material such as EVA, PE or PVC.

In another preferred embodiment the volume of the expansion container is from 10 to 1500 ml, more preferably from 25 to 1000 ml, even more preferably from 50 to 750 ml, and most preferably from 100 to 650 ml. It was found that the first phase of the culturing of the cells, the seeding phase, is preferably carried out in a smaller volume to increase the concentration of the culturing cells. After some time, the number cells are increased and the expansion volume may also be increased. In a preferred embodiment, the expansion container may be adjusted in size. A suitably way of an expansion container to adjust in size is to have a expansion container that contains more than one compartment. Addition of an extra compartment increases the size of the expansion container. In a preferred embodiment, the expansion container comprises at least 2 compartments that may be closed from one another. Suitably, 2, 3, 4, 5 or more compartments are present in the expansion container. Each container may be connected to the other compartments individually. In a more preferred embodiment the expansion container comprises at least 2 compartments, wherein the expansion container is made of a flexible material and the compartments are divided from each other by a means of clamping. Removal of the means of clamping joins the compartments and the size of the expansion container is increased. In a more preferred embodiment, the volume of the expansion container is increased in a step-less manner. A suitable example of increasing the volume in a step-less manner is the use of a roller which gradually unwinds the expansion container, by which the volume is increased gradually.

Preferably in the first stage of the culturing of the cells, the seeding stage, the volume is kept small. This seeding volume is preferably between 10-400 ml which may vary between 10-400 ml in a step-less manner more preferably between 25-300 ml, and most preferably between 50-200 ml. After the cells have increased in number, in the expansion phase, the expansion volume is preferably between 200-1500 ml which can be vary between 100-1500 ml in a step-less manner, more preferably between 300-1000 ml and most preferably between 450-650 ml.

A convenient time point to increase the volume is when the cells have reached at least 50% confluency, more convenient at least 75% confluency, which is usually after 2-9 days, more often after 3-7, and most often after 4-6 days of culturing. Another convenient marker to increase the size of the expansion volume is after more than 80% of the microcarriers are occupied, more preferably at least 85%, most preferably at least 90%. It is also suitable to increase the expansion volume after more than 50% of the microcarriers are occupied, more preferably at least 75%, most preferably at least 90%.

In yet another preferred embodiment the adherent cells, are selected from the group consisting of stem cells, more preferably mesenchymal stem cells. Preferably the biopsy is taken from tissue selected from the group consisting of bone marrow, umbilical cord blood, fat tissue, liver tissue, pancreatic tissue and peripheral blood. A preferred tissue is bone marrow, umbilical cord blood, and peripheral blood as these tissues are fluid and are easy to handle. Most preferred is bone marrow as the amount of stem cells is high.

The purpose of the microcarriers is to provide and increased growing surface for the adherent cells. Therefore in another preferred embodiment, the microcarriers provide a growth surface area from 100 to 60,000 cm$^2$, more preferably a growth surface area from 500 to 40,000 cm$^2$, most preferably a growth surface area from 1000 to 20,000 cm$^2$. It may be clear that as the cells are increasing in number, additional microcarriers may be added to provide enough growth surface area. Depending on the amount of surface area occupied by the adherent cells, microcarriers may be added during the culturing. In addition, fresh medium may be added to the expansion container, and waste medium may be removed. Additional nutrients and/or supplements may be added during the culturing depending on the needs of the cells. In a preferred embodiment, this is done by perfusion. Sensors may be added to the system so that they measure the nutrient level and/or waste level, pH, DO (dissolved oxygen) and the amount of cells in the system. Preferably these sensors operate automatically, more preferably the addition of nutrients and/or supplement is also carried out automatically, most preferably the sensors direct the addition of nutrients and/or supplements.

Preferably in the first volume, during the seeding phase the perfusion rate is 2-20 ml/min, more preferably 5-15 ml/min, most preferably 8-12 ml/min. A perfusion rate between 1-100 ml/min or between 20 and 70 ml/min and even between 30 and 50 m/min is also suitable during the seeding phase. It depends on the amount of non-adherent cells in the biopsy, the perfusion rate is most suitably adjusted to remove small cells, such as red blood cells (RBCs) within 6-12 hours, more suitably within 8-10 hours. Removing small cells, such as red blood cells within 1-48 hours or even within 2 to 35 hours or even within 20 to 30 hours is also suitable.

Preferably when the volume is larger, during the expansion phase the perfusion rate is 1-50 ml/min, more preferably 5-50 ml/min, most preferably 10-24 ml/min. A perfusion rate of 1-200 ml/min, or 75-150 ml/min, and even 90-125 ml/min, during the expansion phase is also suitable. This parameter is set on the dwell time, as the amount of cells increase the consumption rate of nutrients will increase, therefore the dwell time should decrease. To decrease the dwell time, the perfusion rate should increase. In addition the dwell time depends on the volume of the expansion container. Since the volume of the expansion container will increase during the process, the perfusion rate should increase simultaneously. Therefore this parameter will vary during the process.

After the cells have been grown until a desired amount of cells is achieved, the adherent cells may be detached from the microcarriers. The detachment may be done with a suitable detachment agent. Suitable detachment agents may be enzymes, thermo responsive agents and or pH responsive agents. In order to harvest the cells suitably, the adherent cells may be removed through a 50-100 μm filter. The adherent cells will pass through the filter while the microcarriers are retained in the expansion container.

After detachment of the cells from the microcarriers, the cells should be separated from the microcarriers before the cells to start to attach again. Therefore the separation should be done as fast as possible. However, the sheer should remain low enough to maintain cell viability. Preferably during the harvesting phase the perfusion rate is 10-50 ml/min, more preferably 20-40 ml/min, most preferably 25-35 ml/min. A perfusion rate of 1-300 ml/min, or 75-200 ml/min and even 100-150 ml/min, during the harvesting phase is also suitable. The volume of the medium bottle depends on the process time, and the refreshing regime, and whether nutrients can be added in concentrated solutions. Suitable volumes vary from 1-15 liter, more suitable from 2-10 liter. A of volume 1-50 liter or 20-40 liter and even 25-35 liter is also suitable. The time the adherent cells are cultured may also be varied. Preferably at least 10 days are the adherent cells cultured, more preferably from 14 to 21 days. A culture period between 1 and 50 days or between 25 and 40 days and even between 30 and 35 days is also suitable. The process time depends on the amount of adherent cells in the biopsy and the expansion rate of the adherent cells and the required amount of adhered cells It was seen that when a gas volume or headspace is present in the expansion container, due to the moving of the expansion container, extra turbulence is created in the expansion medium. The extra turbulence may cause cells to die or negatively influences cell growth, especially sensitive cells. Therefore in a preferred embodiment, less than 20% headspace, preferably less than 10%, even more preferably no headspace is present in the expansion container. In the present invention, headspace means the percentage of volume of the expansion container containing gas. 20% headspace means that 80% of the expansion container consists of medium with cells and microcarriers.

The present invention is also directed to a device for expanding adherent cells from crude biopsies comprising an expansion container, microcarriers, culture medium and a filter with from 8 to 20 μm pore size.

In a preferred embodiment, the device of the present invention comprises a means to keep the expansion container in motion with and angle of between 30 to 90° and −30 to −90° or a rotating motion. It was found that a simple method of gentle rocking of the expansion container provides for an optimum of growing conditions for adherent cells to grow on microcarriers. Suitably the expansion container is a bag-type of expansion container. Preferably the expansion chamber is moved in such a rocking motion that the microcarriers are allowed to travel from one end of the expansion container to the other end of the expansion container without allowing to settle or sediment. Depending on the volume, amount of microcarriers, size of microcarriers and the amount of cells attached to the microcarriers the rocking angle and speed may vary. A skilled person may optimize the rocking angle and speed and these optimizations are well within his skills. The rocking movement is preferably at least between 30° and −30° when starting from a horizontal position (0°), more preferably between 50° to 90° and −50 to −90°, more preferably between 60° to 80° and −60 to −80°. The rocking movement may go further than 90° and −90° (e.g. rotating), however that creates the same movement as going back from 90° or −90° to the horizontal position (0°). It is to be understood rotating is comparable to a rocking movement between 90° to −90° from the horizontal position and is therefore included in the present invention. The speed of the rocking depends on the expansion volume; smaller expansion volumes require a relatively low rocking speed, whereas larger expansion volumes require a higher rocking speed. For expansion volume between 50 and 200 ml, a rocking speed of between 2 and 10 rpm is suitable, more suitable a rocking speed of between 3 and 8, most suitable between 4 and 6 rpm. In addition, there may be a stop time between and including the maximum/minimum rock angle, i.e. before the expansion container will return. A rocking speed between 1 and 50 rpm, or between 15 and 35 rpm or even between 20 and 30 rpm is also suitable for expansion volume between 50 and 200 ml. In addition, there may be a stop time between and including the maximum/minimum rock angle, i.e. before the expansion container will return. For expansion volume between 100 and 1000 ml 10 to 20 rpm is suitable, more suitable between 12 and 16 rpm, and most suitable between 13 and 15 rpm. In addition, there may be a stop time at the maximum/minimum rock angle, i.e. the before the expansion container will return. A rocking speed between 1 and 100 rpm, or 5 to 50 rpm, and even 7-35 rpm is also suitable for expansion volume between 100 and 1000 ml. The time the expansion container remains at the maximum/minimum rocking angle depends on the settlement time, i.e. it should allow the microcarriers to travel to the lowest point, however, the stop time should not be too long for the microcarriers with the cells attached to stick together and form aggregates. The rocking angle, rocking speed and stop time depends on the sedimentation velocity and may be calculated with the Stokes sedimentation equation, which is well within the skills of a skilled person. A skilled person therefore knows how to optimize these parameters. When the volume is small, e.g. during the seeding phase a relatively slow rocking rate is needed to allow cell attachment. Preferred rocking rates are 1-20°/second, more preferably 5-15°/second, most preferably 7-12°/second. A rocking rate between 1-250°/second, or 20-150°/second, and even 50-100°/second is also suitable during the seeding phase. When the culturing volume is larger, e.g. during the expansion phase a higher rocking rate is needed to prevent formation of microcarrier/cell aggregates and to maintain a homogeneous suspension. Preferred rocking rates are 1-30°/second, more preferred 5-20°/second, and most preferred 10-15°/second. A rocking rate between 1-300°/second, or between 25-250°/second, and even between 50-150°/second is also suitable during the expansion phase. During the harvesting phase a relatively high rocking rate is needed to detach the adherent cells from the microcarriers. Preferred rocking rates are 5-45°/second, more preferred 10-30°/second, and most preferred 15-20°/second. A rocking rate between 1-350°/second, or between 50-250°/second and even between 100-200°/second is also suitable during the harvesting phase.

The acceleration and deceleration represent a part of the rest time which allows to microcarriers to sediment through the container. During the process, the amount of adherent cells per microcarrier will increase. Therefore the microcarrier weight will increase and consequently the sedimentation speed will increase. Therefore, the acceleration and deceleration will vary through the process. When the volume is small, e.g. during the seeding phase a preferred acceleration/deceleration varies between 10-100°/s$^2$, more preferred between 20-70°/s$^2$, most preferred between 35-50°/s$^2$. An acceleration/deceleration between 1-500°/s$^2$, or between 150-400°/s$^2$, and even between 200-300°/s$^2$ is also suitable during the seeding phase. When the culturing volume is larger, e.g. during the expansion phase a preferred acceleration/deceleration varies between 10-150°/s$^2$, more preferred between 20-100°/s$^2$, most preferred between 40-60°/s$^2$. An acceleration/deceleration between 1-700°/s$^2$, or between 200-600°/s$^2$, and even between 300-500°/s$^2$ is also suitable during the expansion phase. During the harvesting phase a preferred acceleration/deceleration varies between 10-100°/s$^2$, more preferred between 20-70°/s$^2$, most preferred between 35-50°/s$^2$. An acceleration/deceleration between 1-990°/s$^2$, or between 200-800°/s$^2$, or between 300-600°/s$^2$, and even between 400-500°/s$^2$ is also suitable during the harvesting phase.

In a preferred embodiment the adherent cells may be present in a crude or cellular biopsy. The device of the present invention comprises several elements which allow the use of a crude or cellular biopsy in a cell expansion. In the present invention crude or cellular biopsy means a biopsy that has a similar cellular composition as the tissue in the organism. Large particles that are present due to the method of obtaining the biopsy may be removed, e.g. large blood clots and or large tissue particles such as bone chips. To remove these large particles suitably a large filter with pore size of 100 µm is used. By using the device of the present invention pre-culturing step is not needed to expand adherent cells. Microcarriers are added to allow the adherent cells to attach. Adherent cells need a surface to grow on. Microcarriers are particles that have a high surface to volume ratio, to allow a large grow surface area for the adherent cells in a small volume. Microcarriers are added either before the addition of the crude biopsy and/or medium but may also be added after the addition of the crude biopsy and/or medium. In a preferred embodiment, the microcarriers are added after the addition of the crude biopsy and medium. After addition of the crude biopsy, preferably fresh medium is passed through the expansion container while simultaneous medium is removed so that a constant volume is maintained. By removing medium from the expansion container through a filter with a pore size between 8 and 20 µm, blood cells and other smaller cells, are removed, and the adherent cells are retained in the expansion container. Preferred filters have a pore size of between 8 and 15 µm, more preferably between 8 and 12 µm, most preferably between 8 and 10 µm. The filtering step may be performed before or after the adherent cells are allowed to attach to the microcarriers. In a preferred embodiment, first a filtering step through an 8-20 µm filter is carried out before allowing the adherent cells to attach to the microcarriers. In a preferred embodiment the entire medium is removed though the 8-20 µm filter. After a few days of culturing, other cells that did not pass through the filter, but also did not attach to the microcarriers may have died and have become smaller; these cells may then also be removed through the 8-20 µm filter. In a preferred embodiment, every medium that is removed from the expansion container is passed through an 8-20 µm filter. In order for the filter to work optimal, the filter preferably is non toxic for the adherent cells to be expanded. Furthermore it is beneficial if the adherent cells do not attach to the filter material.

The cells attached to the microcarriers grow optimal when the microcarriers are kept in a homogeneous suspension are not allowed to settle or sediment. The force to keep the microcarriers in suspension should be such that the microcarriers are not allowed to settle or sediment however, the force should not be too much so to damage the cells. It depends on the expansion container and the microcarriers used what kind of movement and force is used. The microcarriers may be stirred by e.g. a propeller or the container it self may move to prevent the microcarriers from settling. In a preferred embodiment the expansion container is disposable. Suitable disposable container is a so-called culture bag containers. The expansion chamber is preferably a bag type of container. In a preferred embodiment, the expansion chamber is made of flexible material. In a most preferred embodiment the expansion chamber is a disposable bag type container made of flexible material. Suitable disposable material is able to be sterilized. The advantage of having a disposable expansion container is that the expansion container is used only for one person, so that cross-contamination does not occur. It also obviates the need for extensive cleaning between two expansion runs. Suitable disposable material may be EVA, PE or PVC.

Preferably the device according to the present invention comprises an additional filter with a pore size of 50 to 100 µm. In order to harvest the adherent cells, the adherent cells may be first detached from the microcarriers, preferably by a suitable detachment agent. Suitable detachment agents may be enzymes, thermo responsive agents and or pH responsive agents. After detachment, the detached adherent cells are then removed through the filter with pore size of 50 to 100 µm. The adherent cells will pass through the filter while the microcarriers are retained in the expansion container.

In a preferred embodiment the device of the present invention comprises an expansion container having a volume from 10 to 1500 ml, more preferably from 25-1000 ml, even more preferably from 50 to 750 ml, and most preferably from 100 to 650 ml. It was found that the first phase of the culturing of the cells, the seeding phase, is preferably carried in a smaller volume to increase the concentration of the culturing cells. After some time, the number cells are increased and the volume may also be increased. In a preferred embodiment, the expansion container may be adjusted in size. A suitably way of an expansion container to adjust in size is to have a expansion container that contains more than one compartment. Addition of an extra compartment increases the size of the expansion container. In a preferred embodiment, the expansion container comprises at least 2 compartments that may be closed from one another. Suitably, 2, 3, 4, 5 or more compartments are present in the expansion container. Each container may be connected to the other compartments individually. In a more preferred embodiment the expansion container comprises at least 2 compartments, wherein the expansion container is made of a flexible material and the compartments are divided from each other by a means of clamping. Removal of the means of clamping joins the compartments and the size of the expansion container is increased. In a more preferred embodiment, the volume of the expansion container is increased in a step-less manner. A suitable example of increasing the volume in a step-less manner is the use of a roller which gradually unwinds the expansion container, by which the volume is increased gradually.

Preferably in the first stage of the culturing of the cells, the seeding stage, the volume is kept small. This seeding volume is preferably between 10-400 ml which can be vary between 10-400 ml in a step-less manner more preferably between 25-300 ml, and most preferably between 50-200 ml. After the cells have increased in number, in the expansion phase, the expansion volume is preferably between 200-1500 ml which can be vary between 100-1500 ml in a step-less manner, more preferably between 300-1000 ml and most preferably between 450-650 ml.

The purpose of the microcarriers is to provide and increased growing surface for the adherent cells. Therefore in another preferred embodiment, the microcarriers provide a growth surface area from 100 to 60,000 cm$^2$, more preferably a growth surface area from 500 to 40,000 cm$^2$, and most preferably a growth surface area from 1000 to 20,000 cm$^2$.

Additional nutrients and/or supplements may be added during the culturing depending on the needs of the cells. In a preferred embodiment, this is done by perfusion. Sensors may be added to the device of the present invention so that they measure the nutrient level and/or waste level, pH, DO (dissolved oxygen) and the amount of cells in the system. Preferably these sensors operate automatically, more preferably the addition of nutrients and/or supplement is also carried out automatically, most preferably the sensors direct the addition of nutrients and/or supplements.

Preferably in the seeding volume, during the seeding phase the perfusion rate is 2-20 ml/min, more preferably 5-15 ml/min, most preferably 8-12 ml/min. A perfusion rate between 1-100 ml/min, or between 20-70 ml/min and even between 30-50 ml/min is also suitable during the seeding phase. It depends on the amount of non-adherent cells in the biopsy, the perfusion rate is most suitably adjusted to remove small cells, such as red blood cells (RBCs) within 6-12 hours, more suitably within 8-10 hours. Removing small cells, such as red blood cells within 1-48 hours, or even within 2-35 hours and also within 20-30 hours is also suitable.

Preferably when the volume is larger, during the expansion phase the perfusion rate is 1-50 ml/min, more preferably 5-50 ml/min, most preferably 10-24 ml/min. A perfusion rate of 1-200 ml/min, or 75-150 ml/min, and even 90-125 ml/min during the expansion phase is also suitable. This parameter is set on the dwell time, as the amount of cells increase the consumption rate of nutrients will increase, therefore the dwell time should decrease. To decrease the dwell time, the perfusion rate should increase. In addition the dwell time depends on the volume of the expansion container. Since the volume of the expansion container will increase during the process, the perfusion rate should increase simultaneously. Therefore this parameter will vary during the process.

After the cells have been grown until a desired amount of cells is achieved, the adherent cells may be detached from the microcarriers. The detachment may be done with a suitable detachment agent. Suitable detachment agents may be enzymes, thermo responsive agents and or pH responsive agents. In order to harvest the cells suitably, the adherent cells are removed through a 50-100 µm filter. The adherent cells will pass through the filter while the microcarriers are retained in the expansion container.

After detachment of the cells from the microcarriers, the cells should be separated from the microcarriers before the cells to start to attach again. Therefore the separation should be done as fast as possible. However, the sheer should remain low enough to maintain cell viability. Preferably during the harvesting phase the perfusion rate is 10-50 ml/min, more preferably 20-40 ml/min, most preferably 25-35 ml/min. A perfusion rate of 1-300 ml/min, or 75-200 ml/min, an even 100-150 ml/min during the harvesting phase is also suitable. The volume of the medium bottle depends on the process time, and the refreshing regime, and whether nutrients can be added in concentrated solutions. Suitable volumes vary from 1-15 liter, more suitable from 2-10 liter. A of volume 1-50 liter, or 20-40 liter and even 25-35 liter, is also suitable. The time the adherent cells are cultured may also be varied. Preferably at least 10 days are the adherent cells cultured, more preferably from 14 to 21 days. A culture period between 1 and 50 days, or between 25-40 days, and even between 30-35 days is also suitable. The process time depends on the amount of adherent cells in the biopsy and the expansion rate of the adherent cells It was seen that when a gas volume or headspace is present in the expansion container, due to the moving of the expansion container, extra turbulence is created in the expansion medium. The extra turbulence may cause cells to die or negatively influences cell growth, especially sensitive cells. Therefore in a preferred embodiment, less than 20% headspace, preferably less than 10%, even more preferably no headspace is present in the expansion container. In the present invention, headspace means the percentage of volume of the expansion container containing gas. 20% headspace means that 80% of the expansion container consists of medium with cells and microcarriers.

In a preferred embodiment the cells are stem cells, more preferably mesenchymal stem cells, most preferably human mesenchymal stem cells. The gentle rocking of the present invention allows for growth of the stem cells but is gentle enough not to damage the sensitive stem cells or to differentiate the stem cells.

Preferably the adherent cells are from a biopsy taken from tissue selected from the group consisting of bone marrow, umbilical cord blood, fat tissue, liver tissue, and peripheral blood. A preferred tissue is bone marrow, umbilical cord blood, and peripheral blood as these tissues are fluid and are easy to handle. Most preferred is bone marrow as the amount of stem cells is high.

Experimental Section

The purpose was to define the user requirement specifications of a custom made disposable expansion container, preferably a cell-culture-bag. The objective was to develop an innovative automated, closed bioreactor system that is placed on location (in the hospital) with which patient-own adult stem cells can be culture expanded in clinically required quantities (e.g. 50 to 800 million cells). In practice, this system would allow the surgeon to inject a fresh biopsy, e.g. bone marrow aspirate of several cc in the closed bioreactor. The adult stem cells (mesenchymal stromal cells) are then culture expanded in a fully automated fashion so that days to weeks later the cells can be harvested and used for autologous (patient-own) implantation to treat various tissue disorders varying from cardiovascular disease to bone defects.

To reduce space, vulnerability and the cost of the bioreactor system, it is preferred that the required process steps are reduced as much as possible and can be performed with the minimum amount of devices.

General Procedure

2D Culture:

MSC are expanded using 2D cell culture flask, as is used in the prior art.

Preculture Step to Remove Red Blood Cells (Not According to the Invention)

The bone marrow aspirate is seeded in a 2D cell culture flask to select the human mesenchymal stromal cells (hMSCs) by adhesion, after which small cells (e.g. Red blood cells) are removed by flushing.

Preculture of Cells to Obtain a Starting Concentration for Microcarriers

Because a minimum starting concentration of MSCs per square centimeter culture surface is required to be able to expand the MSCs, the MSCs are expanded in the 2D cell culture flask to obtain a sufficient amount of MSC for the volume currently applied cell-culture-bag. When a sufficient amount of MSCs is obtained, the pre-cultured MSCs harvested by a trypsine treatment. It should be noted that with the device of the present invention such a preculture step in 2D tissue culture flasks is not needed.

Expansion of Cells With Microcarriers

Adherent cells are pipetted via the sample port into an expansion container, such as the Xpand cell-culture-bag, in which the cells are allowed to attach to Cytodex 1 microcarriers (+/− 150 µm) placed in the cell-culture bag. After attachment, the MSCs are expanded. Fresh nutrients are supplied from the medium vessel which is pumped though an oxygenator by which the medium is saturated with the required oxygen and carbon dioxide concentration. In the perfusion loop, medium is pumped from the Xpand-cell-culture-bag back into the medium vessel, after which it can be re-saturated with oxygen and carbon-dioxide. Waste medium is pumped into the waste bottle. To make sure no microcarriers (containing the MSCs) are pumped out of the Xpand-cell-culture-bag as results of the perfusion loop, a sedimentation column is placed at the outlet of the bag in which the microcarriers are allowed to sediment back into the bag. In addition, the sedimentation column is equipped with a 100 µm filter so no microcarriers can leave the sedimentation column. Another option is to use an 60 µm filter which is integrated into the Xpand-cell-culture-bag. The microcarriers are kept in suspension by means of an 180° rocking motion (+/−90°) of the cell-culture-bag. To determine MSC growth, analysis is performed by means of sampling, pH and dissolved oxygen measurements. When analysis indicates that the required cell yield is obtained, the MSCs are harvested by pumping a cell dissociation solution into the bag. When the MSCs are dissociated from the microcarriers, they are separated from each other by pumping the MSCs out of the bag while the microcarriers remain in the bag due to the sedimentation column or the integrated 60 µm filter. After separation, the MSC suspension is pumped into a sterile bottle. After manually transfer, they are concentrated by means of a standalone centrifugation. After concentrating the MSCs suspension, it is frozen by manually transport to a standalone freezer. Furthermore, samples are taken to perform analysis manually.

Optimisation to Use of Crude Bone Marrow Aspirate to Expand MSC Cells

It was investigated whether crude bone marrow aspirate may be used without the use of 2D culture flask. The use of 2D culture flask is an extra step in the expansion of cells, requiring extra material, extra transfer steps and thus creating extra risk of infection.

Materials:

TABLE 1

Materials used for the proof of principle

| Process step | Description |
|---|---|
| 1 | Crude aspirate |
| 2 | 100 um cell-strainer |
| 3 + 4 | standard medium |
| 3 + 4 | Cytodex 1 microcarriers |
| 3 | Xpand-cell-culture-bag |
| 3 | Cell-culture-perfusion-hardware |
| 3 | Tubing |
| 3 | Perfusion-loop accessories (t-pieces; check-valve ed) |
| 3 | Male-female connection couples |
| 4 | Gaspermeable cell culture bag |
| 4 | Roto-shake-genie |

| Standard medium | |
|---|---|
| alpha-MEM | 80.98% |
| Foetal bovine serum | 14.57% |
| Penicillin/Streptomycin | 0.89% |
| Ascorbic acid 2-phosphate | 0.89% |
| L-glutamine | 0.89% |
| dexamethasone | 0.89% |
| basic Fibroblast Growth Factor human recombinant | 0.89% |

Analysis of the Crude Aspirate

Due to donor variations, every aspirate is analysed to determine the starting point regarding the total number of nucleated cells.

TABLE 2

Analysis crude aspirate
Analysis of the crude aspirate used for the proof of principle

| Parameter | Value | Unit |
|---|---|---|
| Gender | male | NA |
| Age | 67 | years |
| Volume | 11 | ml |
| Nucleated cell concentration | 7.63E+06 | cells/ml |
| Nucleated cells total | 8.39E+07 | cells total |
| Volume microcarrier suspension used @ 20 cm²/ml | 200 | ml |
| Cells/cm² in microcarrier suspension | 2.10E+04 | cells/cm² |
| % cells/cm² used compared to 2D standard procedure | 4.19 | % |

Transfer of Crude Aspirate

From the crude aspirate large particles that are due to the extraction method (e.g. fat, tissue and coagulated red blood cells) are removed through a 100 µm filter. The biopsy was transferred to the cell-culture-bag, containing 200 ml of Cytodex 1 microcarrier suspension with a concentration of 20 cm²/ml, suspended in standard medium.

Filtration of the Aspirate in the Xpand-Cell-Culture-Bag Integrated in the Perfusion System After pre-filtration to remove aggregates bigger than 100 µm, the aspirate was transferred to the cell-culture-bag. In the cell-culture bag a filter was integrated in the perfusion system to filter out red blood cells (RBCs) smaller than 15 µm. A 15 µm filter is intergraded into the cell-culture-bag. By means of perfusion through the cell-culture-bag, red blood cells and other cell and cell fragments (<15 µm) are pressed through the 15 µm filter while viable nucleated cells (>15 µm) are maintained in the cell-culture-bag. The process settings used for the filtration are represented in table 3.

TABLE 3

Settings used to filter out red blood cells

| Parameter | Value | Unit |
|---|---|---|
| Perfusion pump | 7 | ml/min |
| Volume medium bottle | 900 | ml |
| Perfusion time | 129 | min |
| Rocking angle | 165 (+82.5 and −82.5) | deg. |
| Rocking rate | 9 | 1°/sec |
| Acceleration | 34 | 1/s2 |
| Decceleration | 34 | 1/s2 |

The Xpand-cell-culture-bag is fed with standard medium from the medium bottle. The standard medium is saturated with $O_2$ and $CO_2$ through the oxygenator. The filtrate exiting the Xpand-cell-culture-bag contains RBCs which are collected in the waste-bottle During perfusion the amount of RBCs in the Xpand-cell-culture-bag decreased which can be seen by the decrease of the red colour.

After two hours filtration, the filtrate (waste bottle) and the residue (cell-culture-bag) were visually inspected using the invert microscope. The filtrate contained a high fraction of RBCs. The amount of RBCs in the residue decreased significantly while the nucleated cells are attached to the microcarriers.

Filtering of Crude Biopsy Through a 5 μm Filter and a 15 μm Filter.

Crude bone marrow biopsy from which large particles such as bone chips and fat globules are removed is diluted in 2D human mesenchymal stem cells expansion medium comparatively to the dilution which was obtained during the filtration in an Xpand-cell-culture-bag.

| Analysis of the crude human bone-marrow biopsy used for filtration through 5 micron vs. 15 micron filter | | |
|---|---|---|
| Parameter | Value | Unit |
| Volume | 4.2 | ml |
| Nucleated cell concentration | 5.63E+06 | cells/ml |
| Nucleated cells total | 2.37E+07 | cells total |
| Volume cell suspension to be filtrated | 50 | ml |
| X nucleated cells for filtration | 4.66E+06 | cells |
| Volume crude human bone-marrow biopsy needed for filtration | 828 | μl |

The diluted biopsy was divided over two 50 ml syringes which were applied as funnels and were connected to the 5 and the 15 micron filter houses. The cell suspension was filtrated by gravity and the filtration period was monitored. In another experiment the diluted crude-human-bone-marrow biopsy was divided over two 50 ml syringes connected to the 5 and the 15 micron filter houses. By adding manual pressure, the entire cell-suspensions were filtrated. The amount of red blood cells in the filtrate was determined by cell counting using the Burker-Tiirk hemocytometer. After filtration, the residue was obtained by means of back-flushing the filters with 50 ml 2D human mesenchymal stem cells expansion medium. The filtrate and the residue from both filters were cultured in 2D culture flasks. After 15 days culture the 2D culture flasks were harvested for cell counting to determine human mesenchymal stem cells loss due to filtration. As control, 828 μl of non-filtrated biopsy was re-suspended in 50 ml 2D Human mesenchymal stem cells expansion medium and cultured simultaneously.

Results and Discussion

Filtration by Gravity

The filtration period was monitored and is represented in attachment 1 and table 2:

TABLE 2

| Filtration by gravity | | | |
|---|---|---|---|
| 5 micron filter | | 15 micron filter | |
| Time (h:m:s) | Volume filtrated (ml) | Time (h:m:s) | Volume filtrated (ml) |
| 00:13:29 | 11 | 00:10:51 | 42 |
| 00:22:07 | 12 | 00:19:28 | 45 |
| 00:33:48 | 14 | 00:31:09 | 48 |
| 00:42:37 | 15 | 00:39:59 | >49 |
| 00:52:41 | 16 | 00:50:02 | >49 |
| 01:30:25 | 18 | 01:27:47 | 50 |
| 02:17:29 | 19 | 02:14:50 | 50 |
| 17:22:44 | 31 | 17:20:05 | 50 |
| 19:52:27 | 35 | 19:49:49 | 50 |

Based on the results represented in table 2 it may be concluded that the filtration period needed to filter a crude-bone-marrow biopsy by gravity using a 15 micron filter is significantly shorter than the filtration period needed using a 5 micron filter.

After a filtration period of 00:10:51, 42 ml of the cell suspension was filtrated through the 15 micron filter. After a filtration period of 19:52:27, 35 ml of the cell suspension was filtrated through the 5 micron filter. This indicates that the filtration period using the 15 micron filter is at least 110 times faster compared to the 5 micron filter. Thus after 1 hour all of the cell suspension was filtered with the 15 micron filter while only 16 ml, which is less than one third of the total volume was filtered with the 5 micron filter. Even after 20 hours still not all of the cell suspension had passed the filter.

When using a volume of about 500 ml, which is the suitable volume to expand human mesenchymal stem cells, e.g. with the Xpand cell culture bag, using a 15 micron filter, the filtration period is about 2 hours to filter out approximately 90% of the red blood cells. When using a 5 micron filter, the filtration period would at least be increased to 219 hours (=at least 9 days). The relatively long filtration period would increase the process time to obtain expanded human mesenchymal stem cells for clinical applications. In addition, cell viability will most likely be negatively influenced by the relatively long filtration period.

This result indicates that the 5 micron filter is unsuitable to filter a crude-human-bone-marrow biopsy.

Filtration by Adding Manual Pressure

During filtration, a relatively high pressure was needed to filter the crude human bone-marrow biopsy through the 5 micron filter. After filtration the amount of red blood cells in the filtrate was determined by diluting the filtrate 10 times with PBS. The yield of Red blood cells obtained in the filtrate was comparable for both filter, see table 3

TABLE 3

| Yield of Red blood cells obtained in the filtrate obtained by filtration by adding manual pressure | | |
|---|---|---|
| Parameter | Value | Unit |
| Amount of Red blood cells in filtrate 5 micron filter | | |
| Sample 1 | 7.20E+07 | Red blood cells |
| Sample 2 | 6.25E+07 | Red blood cells |
| Avarage | 6.73E+07 | Red blood cells |
| Amount of Red blood cells in filtrate 15 micron filter | | |
| Sample 1 | 6.68E+07 | Red blood cells |
| Sample 2 | 6.98E+07 | Red blood cells |
| Avarage | 6.83E+07 | Red blood cells |

After filtration the following 2D cultures were cultivated:

TABLE 4

| 2D cultures after filtration 2D cultures to determine human mesenchymal stem cells loss due to filtration | | |
|---|---|---|
| T-flask | Cell-suspension | Volume (ml) |
| 5 micron filter | | |
| T-175 | Filtrate | 50 |
| T-175 | Residue | 50 |

TABLE 4-continued 2D cultures after filtration
2D cultures to determine human mesenchymal stem cells loss due to filtration

| T-flask | Cell-suspension | Volume (ml) |
|---|---|---|
| | 15 micron filter | |
| T-175 | Filtrate | 50 |
| T-175 | Residue | 50 |
| | Control | |
| T-175 | 828 µl Unfiltrated biopsy | 50 |

After 15 days culture the 2D culture flask were harvested for cell counting to determine human mesenchymal stem cells loss due to filtration. The results are represented in table 5.

TABLE 5 percentage human mesenchymal stem cells loss due to filtration based on 2D cultures described in table 4
human mesenchymal stem cells loss due to filtration based on 2D cultures

| | Control | |
|---|---|---|
| x cells/ml counted | average | x cells total |
| 1.47E+05 | 1.50E+05 | 1.35E+06 |
| 1.53E+05 | | |
| 1.49E+05 | | |

| x cells/ml counted | average | cells total |
|---|---|---|
| | 5 micron filter | |
| | Residue | |
| 5.60E+03 | 5.20E+03 | 4.68E+04 |
| 5.52E+03 | | |
| 4.48E+03 | | |
| | Filtrate | |
| 7.60E+02 | 8.53E+02 | 7.68E+03 |
| 1.24E+03 | | |
| 5.60E+02 | | |
| Percentage filtrate | 14.1% | |
| Percentage residue compared to control | 3.5% | |
| human mesenchymal stem cells loss | 96.5% | |
| | 15 micron filter | |
| | Residue | |
| 7.75E+04 | 7.90E+04 | 7.11E+05 |
| 7.82E+04 | | |
| 8.13E+04 | | |
| | Filtrate | |
| 1.38E+04 | 1.44E+04 | 1.30E+05 |
| 1.40E+04 | | |
| 1.54E+04 | | |
| Percentage filtrate | 15.5% | |
| Percentage residue compared to control | 52.8% | |
| human mesenchymal stem cells loss | 47.2% | |

The results represented in table 5 indicate that:

A comparable percentage of human mesenchymal stem cells were obtained in the filtrate (14.1% for the 5 micron filter and 15.5% for the 15 micron filter)

A higher cell yield was obtained in the residue of the 15 micron filter compared to the residue of the 5 micron filter (52.8% for the 15 micron filter compared to the control culture, 3.5% for the 5 micron filter compared to the control culture)

More than 50% compared to the control cells were obtained with the 15 micron filter while only 3.5% compared to control with the 5 micron filter. This result was confirmed by visual inspection. It should be noted that when a 15 micron filter is integrated in to an cell-culture-bag, as in the Xpand-cell-culture-bag, the back-flush procedure it is not necessary, due to the design of the cell-culture-bag. Therefore, higher human mesenchymal stem cells yield are expected during filtration in the Xpand-cell-culture-bag.

Overall, it may be concluded that the 15 micron filter is suitable for the filtration of a crude-human-bone-marrow biopsy. The 5 micron filter is not suitable for the filtration of a crude-human-bone-marrow biopsy as it does not result in acceptable yield of viably human mesenchymal stem cells within an acceptable process time.

Filtration With an 8 Micron Filter

For the filtration of a cellular-crude-human-bone-marrow-biopsy, BD Falcon cell culture Inserts with an integrated 8 µm filter were used. The Physical specifications BD Falcon cell culture Inserts are represented in table 1:

TABLE 2.1.1

Physical specifications BD Falcon cell culture Inserts

| Description | Specification for 6-well plate insert |
|---|---|
| Effective diameter of membrane | 23.1 mm |
| Effective growth area of membrane | 4.2 cm$^2$ |
| Insert height | 17.2 mm |
| Distance from membrane to bottom of the well | 0.9 mm |
| Suggested media in insert | 1.5-2.5 ml |
| Suggested media in well | 2.7-3.2 ml |
| Growth area in plate well | 9.6 cm$^2$ |
| Material | Track-etched polyethylene terephthalate (PET) |

Analyses and Pre-Treatment of the Cellular-Crude-Human-Bone-Marrow-Biopsy

Due to donor variations, the cellular-crude-human-bone-marrow-biopsy was analysed to determine the starting point regarding the total number of nucleated cells. The cellular-crude-human-bone-marrow-biopsy was pre-filtrated though a 100 µm cell-strainer to remove aggregates bigger than 100 µm (eg. fat, tissue and coagulated red blood cells). The filtrate (e.g. non coagulated nucleated cells and red blood cells) was diluted in human mesenchymal stem cells 2D expansion medium at a concentration of 2.50E06 cells/ml.

TABLE 2.1.2

Analysis of the cellular-crude-human-bone-marrow-biopsy
Analysis of the cellular-crude-human-bone-marrow-biopsy, experiment 1

| Parameter | Value | Unit |
|---|---|---|
| Volume | 19 | ml |
| Nucleated cell concentration | 1.49E+07 | cells/ml |
| Nucleated cells total | 2.83E+08 | cells total |

TABLE 2.1.2-continued

Analysis of the cellular-crude-human-bone-marrow-biopsy
Analysis of the cellular-crude-human-bone-marrow-biopsy, experiment 1

| Parameter | Value | Unit |
|---|---|---|
| Dilution @ 2.500E6 cells/ml human mesenchymal stem cells 2D expansion medium | 113 | ml |

Filtration of the Cellular-Crude-Human-Bone-Marrow-Biopsy

As control to the experimental conditions, the cellular-crude-human-bone-marrow-biopsy, which was only pre-filtrated though a 100 µm cell-strainer to remove aggregates bigger than 100 µm, was cultured along with the experimental was cultured along with the experimental cultures. A fraction of the diluted cellular-crude-human-bone-marrow-biopsy was seeded directly in a 6-well-cultureplate, without filtration through an 8 µm filter. The control culture was not filtrated through an 8 µm filter thus a co-culture of nucleated cells and red blood cells was obtained. After 6 days culture, human mesenchymal stem cells attached to the culture surface of the 6-well-culture-plate, while red blood cells were maintained in suspension. By withdrawing the medium from the 6-well-culture-plate, the human mesenchymal stem cells were physically separated from the red blood cells.

During this experiment, a fraction of the diluted cellular-crude-human-bone-marrow-biopsy was filtrated through an 8 µm filter to physically separate the red blood cells from the human mesenchymal stem cells. The fraction of the diluted cellular-crude-human-bone-marrow-biopsy used for the experimental culture was equal to the fraction used for the control culture.

The materials used for the filtration were 6-well-plate-inserts with integrated 8 µm filter from BD Falcon in combination with 6-well-culture-plates. Blockage of the filter was prevented by filtering dynamically by means of a rocking plateau. The filters containing the diluted cellular-crude-human-bone-marrow-biopsy were placed in the CO2-incubator on a rocking plateau rocking at 5 rpm with an angel of 15 degree.

After filtration, the red blood cells smaller than 8 µm were obtained in the filtrate and the human mesenchymal stem cells bigger than 8 µm were retained by the filter. The residue, containing the human mesenchymal stem cells, was obtained by flushing the filter, 2, 3 and 4 times. The residue was cultured to determine the human mesenchymal stem cells yield. To determine the human mesenchymal stem cells loss in the filtrate, the filtrate was cultured simultaneously. All culture procedures and cell-culture equipment were equal for the control cultures and the experimental cultures.

After 1 hour filtration, a 6-well-culture-plate with the following set-up was incubated:

TABLE 2.1.3 arrangement 6-well plates, after 1 hour filtration
Arrangement 6-well-culture-plates, after 1 hour filtration

| Control: | filtrate: | Filter: |
|---|---|---|
| unfiltered cell suspension | red blood cells cell <8 µm | Remaining human mesenchymal stem cells |
| Residue after flushing the filter two times: human mesenchymal stem cells >8 µm | Residue after flushing the filter for the third time: human mesenchymal stem cells >8 µm | Residue after flushing the filter for the fourth time: human mesenchymal stem cells >8 µm |

All the cultures were refreshed after 6 days culture. By refreshing the medium, the human mesenchymal stem cells from the control culture were physically separated from the red blood cells in suspension.

The 6-well-culture-plates were cultured for 11 days after which the human mesenchymal stem cells yields were determined by harvesting and counting the human mesenchymal stem cells.

Results and Discussion

After 6 days culture, all the cultures were refreshed and visual inspection was performed.

Some colonies and stretched cells were observed in the control culture although the amount was visibly lower than the human mesenchymal stem cells yield obtained from the residue of the filter, after flushing twice. Furthermore, it could be observed that a lot of red blood cells were attached to the colonies of the control culture, resulting in a relatively un-healthy cell-morphology After 11 days culture the human mesenchymal stem cells yield was determined, see table 2.1.4:

TABLE 2.1.4 human mesenchymal stem cells yield control culture and experimental cultures
human mesenchymal stem cells yield

|  | cells per well |
|---|---|
| Control | 5.33E+03 |
| Experimental cultures: |  |
| Filtrate | 3.30E+02 |
| Residue, after flushing the filter two times | 1.51E+05 |
| Residue, after flushing the filter for the third time | 6.86E+03 |
| Residue, after flushing the filter for the fourth time | 7.36E+03 |
| Well containing filter | 4.63E+03 |
| Filter, after flushing | 7.40E+04 |
| Total human mesenchymal stem cells yield from filtrated biopsy | 2.44E+05 |
| Percentage experimental cultures vs. Total human mesenchymal stem cells yield from filtrated biopsy | NA |
| % Filtrate | 0.1 |
| % Residue flush 2 times | 61.9 |
| % Residue flushed 3th time | 2.8 |
| % Residue flushed 4th time | 3.0 |
| % well containing filter | 1.9 |
| % Filter vs. Total from filter | 30.3 |
| % Control vs. Residue, after flushing the filter 2 times | 3.5 |
| % Control vs. Total human mesenchymal stem cells yield from filtrated biopsy | 2.2 |

These results indicate that:

A negligible fraction of human mesenchymal stem cells were lost in the filtrate (0.1%)

A high fraction of human mesenchymal stem cells were obtained after flushing the filter twice (61.9%)

Negligible fractions of human mesenchymal stem cells were obtained after flushing a third and a fourth time (total 5.8%)

However, a high fraction of human mesenchymal stem cells were obtained from the filter (30.3%), indicating a higher human mesenchymal stem cells yield can be obtained by means of a system in which it is not necessary to flush the filter, like the Xpand-cell-culture-bag.

The human mesenchymal stem cells yield obtained from the control culture was negligible compared to the amount of human mesenchymal stem cells obtained from the Residue, after flushing the filter 2 times (3.5%)

These observations indicate that it is feasible to physically separate human mesenchymal stem cells (hMSCs) from red blood cells by means of filtration using an 8 µm, without losing hMSCs in the process. The hMSCs yield is increased significantly by isolating hMSCs from a cellular-crude-human-bone-marrow-biopsy prior to culture. The hMSCs yield obtained after flushing the filter two times was 28 fold higher compared to the control culture. In addition, a healthier cell-morphology is obtained The hMSCs yield can be further increased by means of a system in which it is not necessary to flush the filter, like the Xpand-cell-culture-bag.

Expansion in Culture Bags

In this experiment expansion of cells in 2D culture flask were compared to 3D culture bags. Gas-permeable-cell-culture-bags were used for the 3D cultures on Cytodex 1 microcarriers. The gas-permeable-cell-culture-bags were placed on a rotating platform (which is comparable to a 180° rocking angle). The gas-permeable-cell-culture-bag was incubated in a CO2-incubator at 37° C. and 5% $CO_2$.

Analyses of the Cellular-Crude-Human-Bone-Marrow-Biopsy

Due to donor variations, the cellular-crude-human-bone-marrow-biopsy was analysed to determine the starting point regarding the total number of nucleated cells. The cellular-crude-human-bone-marrow-biopsy was pre-filtrated though a 100 μm cell-strainer to remove aggregates bigger than 100 μm (e.g. fat, tissue and coagulated red blood cells). The filtrate (e.g. non coagulated nucleated cells and red blood cells) was diluted in human mesenchymal stem cells 2D expansion medium at a concentration of 2.50E06 cells/ml.

TABLE 2.2.1

Analysis of the cellular-crude-human-bone-marrow-biopsy

| Parameter | Value | Unit |
|---|---|---|
| Volume | 14.35 | ml |
| Nucleated cell concentration | 1.14E+07 | cells/ml |
| Nucleated cells total | 1.92E+08 | cells total |
| Dilution @ 2.500E6 cells/ml human mesenchymal stem cells 2D expansion medium | 76.8 | ml |

Filtration of the Cellular-Crude-Human-Bone-Marrow-Biopsy

As control to the experimental conditions, the cellular-crude-human-bone-marrow-biopsy, which was pre-filtrated though a 100 μm cell-strainer to remove aggregates bigger than 100 μm, was cultured along with the experimental cultures. A fraction of the diluted cellular-crude-human-bone-marrow-biopsy was seeded directly, without filtration through an 8 μm filter, in a T-75 culture flask for the 2D control. For the 3D control culture a fraction of the diluted cellular-crude-human-bone-marrow-biopsy was seeded directly into a gas-permeable-cell-culture-bag containing Cytodex microcarriers, without filtration through an 8 μm filter.

The control cultures were not filtrated through an 8 μm filter thus a co-culture of nucleated cells and red blood cells was obtained. After 6 days culture, human mesenchymal stem cells attached to the culture surface of the T-75 culture flask or Cytodex 1 microcarriers, while red blood cells were maintained in suspension. By withdrawing the medium from the cultures, the human mesenchymal stem cells were physically separated from the red blood cells. The fractions of the diluted cellular-crude-human-bone-marrow-biopsy used for control cultures were equal to the fractions used for the experimental cultures. All culture procedures and cell-culture equipment were equal for the control cultures and the experimental cultures.

During this experiment, a fraction of the diluted cellular-crude-human-bone-marrow-biopsy was filtrated through an 8 μm filter to physically separate the red blood cells from the mesenchymal stem cells. The materials used for the filtration were 6-well-plate-inserts with integrated 8 μm filter from BD Falcon in combination with 6-well-culture-plates. Blockage of the filter was prevented by filtering dynamically by means of a rocking plateau. The filters containing the diluted cellular-crude-human-bone-marrow-biopsy were placed in the CO2-incubator on a rocking plateau rocking at 5 rpm with an angel of 15 degree. After filtration, the red blood cells smaller than 8 μm were obtained in the filtrate and the human mesenchymal stem cells bigger than 8 μm were blocked by the filter. The residue, containing the human mesenchymal stem cells, was obtained by flushing the filter two times.

The residue was cultured in a T-75 culture flask for the 2D control and in a gas-permeable-cell-culture-bag cultured in a CO2-incubator containing Cytodex microcarriers for the 3D control.

In addition, a fraction of the diluted cellular-crude-human-bone-marrow-biopsy was used to isolate the human mesenchymal stem cells by means of centrifugation. The centrifuge works using the sedimentation principle, where the centripetal acceleration causes particles with a relatively high density (e.g. human mesenchymal stem cells) to separate out along the radial direction (the bottom of the centrifuge tube). By the same token, particles with a relatively low density (e.g. red blood cells) will tend to move to the top. By subtracting the top layer, red blood cells and human mesenchymal stem cells were psychically separated.

The remainder suspension from the bottom of the centrifuge tube was re-suspended. The obtained cell-suspension was cultured in T-75 culture flask for the 2D control and in a gas-permeable-cell-culture-bag containing Cytodex microcarriers for the 3D control.

In summary, human mesenchymal stem cells were isolated and cultured accordingly:

| | Isolation and culture conditions | |
|---|---|---|
| Condition | 3D (10 ml gas-permeable-cell-culture-bag) | 2D (15 ml T-75 culture flask) |
| 1 | Control | Control |
| 2 | Filtrated culture | Filtrated culture |
| 3 | Centrifuged culture | Centrifuged culture |

Isolation and culture conditions

The following parameters were applied:

| Parameters applied during | |
|---|---|
| Parameters: | Setting: |
| 2D: Standard conditions | |
| Starting volume: | 15 ml |
| Seeding density: | 5.00E05 cells/0.2 ml |
| First refreshment | After 6 days |
| Second refreshment | 3-4 days |
| 3D: | |
| Starting volume: | 10 ml |
| Microcarrier density: | 20 $cm^2$ microcarrier/ml medium |
| Rocking regime during seeding: | Rotating continuously at minimum rocking rate (+/−5 rpm) |
| Seeding density: | 5.00E05 cells/0.2 ml → excluding cell loss due to treatment |
| First refreshment | After 6 days |
| Second refreshment | 3-4 days |

Parameters and settings experiment 2

Cell attachment and growth in the cell-culture-bags were monitored by means of visual inspection.

Results and Discussion

After 6 days culture, all the cultures were refreshed and visual inspection was performed.

Visual inspection of the 2D cultures indicated that the highest human mesenchymal stem cells yield and the most viable human mesenchymal stem cells morphology were obtained in the filtrated culture. It was visible that the amount of red blood cells decreased by washing, however, the filtering procedure was clearly more effective.

Visual inspection of the 3D cultures indicated that the highest human mesenchymal stem cells yield and the most viable morphology were obtained in the filtrated culture. Cell-aggregates were formed in the control culture and the centrifuged culture, even though the amount of red blood cells was reduced by centrifugation. These observations indicate that human mesenchymal stem cells need to be isolated completely prior to 3D culture using Cytodex 1 microcarriers.

After 10 days culture, all the cultures were refreshed and visual inspection was performed.

Visual inspection of the 2D cultures indicated human mesenchymal stem cells expansion in all cultures. However, the highest human mesenchymal stem cells yield and the most viable morphology were obtained in the filtrated culture. Confirming the results obtained during experiment 1 described in section 2.1.

Visual inspection of the 3D cultures indicated expansion of cell-aggregates in the control culture and the centrifuged culture. No stretched human mesenchymal stem cells were observed in contrast to the filtrated culture were a lot of healthy stretched human mesenchymal stem cells were observed.

These observations indicate that in prior art procedures, human mesenchymal stem cells need to be isolated completely prior to 3D culture using Cytodex 1 microcarriers. By means of the standard 2D isolation procedure based on adherence this means that a 2D isolation step of 6 days is needed prior to 3D culture on Cytodex microcarriers. The isolation of mesenchymal stem cells can be obviated by using a filter between 8 and 20 µm and expansion of crude cellular biopsies is feasible to culture directly on Cytodex 1 microcarriers.

Filtration of a Crude-Human-Bone-Marrow-Biopsy Through a 40 Micron Filter.

The results described above indicated that is not feasible to physically separate human mesenchymal stem cells from red blood cells by means of filtration using a 100 µm. In addition it has been demonstrated that the human mesenchymal stem cells yield is increased significantly by isolating the human mesenchymal stem cells from a cellular-crude-human-bone-marrow-biopsy prior to culture.

Procedure

A crude-human-bone-marrow-biopsy was filtrated through a 40 micron filter. Before and after filtration, visual inspection was performed. In addition, the amount of nucleated cells in the biopsy was counted before and after filtration. This was done to indicate the efficiency of the filtration procedure using a 40 micron filter.

Results and Discussion

Before and after filtration, visual inspection was performed to visualize the cellular mixture of wanted cells (human mesenchymal stem cells) and unwanted cells (e.g. red blood cells).

Visual inspection clearly indicates that is not feasible to physically separate human mesenchymal stem cells from red blood cells by means of filtration using a 40 µm.

These observations were confirmed by cell counting since the amount of nucleated cells before filtration was comparable to the amount of nucleated cells after filtration, see table 2.3.1.

| Cell counting before and after filtration of a crude-human-bone-marrow-biopsy through a 40 micron filter | | |
|---|---|---|
| Parameter | Value | Unit |
| Before filtration | 6.98E+07 | cells total |
| After filtration | 6.75E+07 | cells total |
| Percentage nucleated cells isolated by filtration | 3.2 | % |

The results obtained by cell counting clearly indicate that a negligible amount of nucleated cells were isolated after filtration through a 40 micron filter. From these results can be concluded that filtration crude-human-bone-marrow-biopsy through a 40 micron filter is not sufficient for the isolation of human mesenchymal stem cells.

Conclusions

The described results indicate that:

It is not feasible to physically separate human mesenchymal stem cells from red blood cells by means of filtration using a 40-100 µm filter.

It is feasible to physically separate human mesenchymal stem cells from red blood cells by means of filtration using an 8 µm, without losing human mesenchymal stem cells in the process.

The hypothesis that the standard 2D culture procedure may be optimized by separating the human mesenchymal stem cells from the red blood cells prior to culture was confirmed. The human mesenchymal stem cells yield is increased significantly by isolating the human mesenchymal stem cells from a cellular-crude-human-bone-marrow-biopsy prior to culture. The human mesenchymal stem cells yield obtained after flushing the filter two times was 28 fold higher compared to the control culture. In addition, a healthier cell-morphology is obtained.

Since the filter was not flushed effectively, the human mesenchymal stem cells yield can be further increased by means of a system in which it is not necessary to flush the filter, like the Xpand-cell-culture-bag.

By means of centrifugation the concentration of red blood cells can be decreased. However, the filtering procedure was clearly more effective.

Cell-aggregates were formed in the control culture and the centrifuged culture, even though the amount of red blood cells was reduced by centrifugation. No stretched human mesenchymal stem cells were observed in contrast to the filtrated culture were a lot of healthy stretched human mesenchymal stem cells were observed.

Therefore it can be concluded that red blood cells need to be removed prior to 3D culture using Cytodex 1 microcarriers.

By means of the standard 2D isolation procedure based on adherence this means that a 2D isolation step of 6 days is needed prior to 3D culture on Cytodex microcarriers. By means of filtration it is feasible to culture directly on Cytodex 1 microcarriers.

Using the filtering with a poresize of 8-20 µm crude cellular biopsies may be cultured directly in a 3D expansion vessel, such as the Xpand culture bag. Filtering removes the need for preculture in the standard 2D procedure which takes about 6 days to remove the red blood cells. With filtering through a poresize of 8-20 µm the process time and process steps are decreased while the human mesenchymal stem cells yield is increased.

Expansion of Aspirate on Cytodex 1 Microcarriers

Visual inspection during filtration indicated that air was pumped into Xpand-cell-culture-bag during perfusion. The air causes high sheer which negatively influences cell viability. These observations confirm that the headspace should be lower than 20%. Therefore, the expansion of the aspirate, of which large particles, >100 μm were removed, was carried out in a gas-permeable-cell-culture-bag which was placed on a rotating platform (which is essentially a −90° to 90° rocking angle). The gas-permeable-cell-culture-bag was placed in a $CO_2$-incubator. The rotating platform was set on 5 rpm. During the expansion phase, the medium was refreshed every 3 days.

After 14 days culture, visual inspection using the invert microscope indicated that the nucleated cells attached to the Cytodex 1 microcarriers expanded. After 14 days culture a sample was taken from the gas-permeable-cell-culture-bag to determine the amount of attached cells by harvesting and counting, see table 4:

TABLE 4

Calculations regarding the amount of attached cells. after 14 days expansion of the aspirate
Day 14: harvest of cells to determine amount of attached cells

| | | |
|---|---|---|
| Count coulter counter 50 x diluted: | 8.75E+04 | cells total sample |
| Total gas-permeable-cell-culture-bag would contain: | 1.58E+06 | cells total gas-permeable-cell-culture-bag |
| Gas-permeable-cell-culture-bag contained 18 ml @ 20 $cm^2$/ml = 3.60E+02 $cm^2$ | 4.38E+03 | cells/$cm^2$ gas-permeable-cell-culture-bag |
| Total Xpand-cell-culture-bag would contain: | 1.75E+07 | cells total Xpand cell-culture-bag |
| Xpand-cell-culture-bag contained 200 ml @ 20 $cm^2$/ml = 4.00E+03 $cm^2$ | 4.38E+03 | cells/$cm^2$ Xpand-cell-culture-bag |

Although the harvest efficiency of the sample was lower than a 100%, these calculation indicate that if the aspirate was expanded in the Xpand-cell-culture-bag under the same expansion settings, that the Xpand-cell-culture-bag would at least contain 1.75E+07 expanded mesenchymal stem cells.

Optimization of the Process:

The yield of 1.75E+07 mesenchymal stem cells may be optimized by optimizing the process settings and culture conditions.

Aspirate

The aspirate used for the proof of principle contained a relatively low amount of nucleated cells compared to the average aspirate which is based on a database of 40 aspirates:

TABLE 5 average aspirate which is based on a database of 40 aspirates
Average aspirate which is based on a database of 40 aspirates

| | |
|---|---|
| Average cell concentration (cells/ml) | 2.03E+07 |
| Average volume (ml) | 14.5 |
| Average amount of nucleated cells | 2.53E+08 |

The aspirate used during the described experiment contained 8.39E+07 nucleated cells. This is 33% of the average aspirate. This indicates that 5.27E+07 mesenchymal stem cells may be obtained from an average aspirate Refreshment Regime During the described experiment, the medium was refreshed every 3 days. An experiment comparing daily refreshment to the refreshment regime used during this experiment, on 2D culture in T-flaks, indicated that the expansion can be optimized to 183%, see FIG. 1:

These results indicate that an average aspirate may be expanded to 1.45E+08 Mesenchymal stem cells total, when standard medium containing supplements is used and refreshed daily.

Culture Period

The culture period may be prolonged to 21 days of culture. At a minimal cell growth of 1 doubling every 3 days, an average aspirate may be expanded to 5.79E+08 Mesenchymal stem cells total, when it is cultured for 21 days, with standard medium containing supplements which is refreshed daily.

Rocking Angle

The rocking angle is based on the quality of the microcarrier suspension which should be homogeneous.

TABLE 6

Experiments regarding optimal rocking angle
Minimum required rocking angle based on past experiments

| Experiment | Rocking angle (deg.) | Quality of the microcarrier suspension<br>+ = good<br>+/− = acceptable<br>− = bad |
|---|---|---|
| Rocking plateau 1 | −4.5/+4.5 | − |
| Rocking plateau 2 | −15/+15 | − |
| Rocking plateau 3 | Rotating = comparable to −90/+90 | + |
| Rocking plateau 4 | −45/+45 | +/− |
| Rocking plateau 4 | −60/+60 | +/− |

Conclusions

The results indicated that it is feasible to physically separate mononuclear cells from red blood cells by filtration, using an 8 or 15 μm filter, without losing mesenchymal stem cells in the process. This obviates the need to use 2D culture flasks. It was also found that when a sufficient filter area is integrated it is not blocked due to the applied rocking motion.

Because a minimum starting concentration of mesenchymal stem cells per square centimeter culture surface is required to be able to expand the mesenchymal stem cells, the seeding volume is preferably relatively low compared to the expansion volume. To be able to seed the crude aspirate in the same bag as the selected mesenchymal stem cells will be expanded, it is suggested to increase the volume of the Xpand-cell-culture-bag after the seeding phase. This may be feasible by increasing the volume of the Xpand-cell-culture-bag step-less by means of a clamping system, which can be removed after seeding to obtain a compartment with an increased volume. It is also possible to increase the volume of the expansion container in a step-less manner. A suitable example of increasing the volume in a step-less manner is the use of a roller which gradually unwinds the expansion container, by which the volume is increased gradually.

A second perfusion pump or a flow controller always had a deviation of +/−0.5% with the first perfusion pump or flow controller. If the perfusion pressure before and after the bag are not exactly the same, the Xpand-cell-culture-bag will be drained or explode in time. It is useful to design the cells-culture-bag in such way that the perfusion loop is not influenced by gravity. Possible ways are (i) When the outlet is located at the centre of the bag and is assembled in a vertical position, the influence of gravity on the perfusion loop will be minimized since gravity pressure prefers to move in horizontal direction. (ii) a check-valve, which only allows flow in the desired direction, could be placed at the inlet of the Xpand-cell-culture-bag to prevent microcarriers to exit the bag via the inlet.

It would be preferred to be able to expand and harvest the mesenchymal stem cells without the needs of a sedimentation column. This is achievable when a larger pore size filter is integrated into the cell-culture bag. Preferably the filter has a filter size of between 50 and 100 μm. These filters will allow the desired cells to pass without any effort but will keep the microcarriers inside the bag. In addition, it is advantageous to apply a sufficiently large filter area to prevent the filter from blocking. In combination with the applied rocking motion, the risk that the filter is blocked becomes even smaller. Furthermore it is useful if the filter material does not allow cell attachment.

It has been determined that it may be feasible to concentrate the obtained mesenchymal stem cells suspension automatically in the closed system by means of the BioSep 10L ASP 990 from Applikon. The mesenchymal stem cells suspension can then be pumped through a BioSep system from Applikon (based on ultrasonic separation), to be concentrated before transfer into a sterile clinical device. Therefore, the BioSep 10L ASP 990 from Applikon may be applied to concentrate the cell-suspension. However, another system may also be integrated into the system.

Experiments showed that the seeding volume is most valuable between 20-100 ml, while the expansion volume is most favorable between 100 and 750 ml. It was further shown that the expansion of mesenchymal stem cells may be further optimized by addition of supplements, and by refreshing the medium daily instead of every 3 days. Furthermore it is feasible to culture the cells for 21 days, thereby even further optimizing the expansion. An average aspirate may be expanded to 5.79E+08 mesenchymal stem cells total, when it is cultured for 21 days, with -standard medium containing supplements which is refreshed daily.

Figure 2:
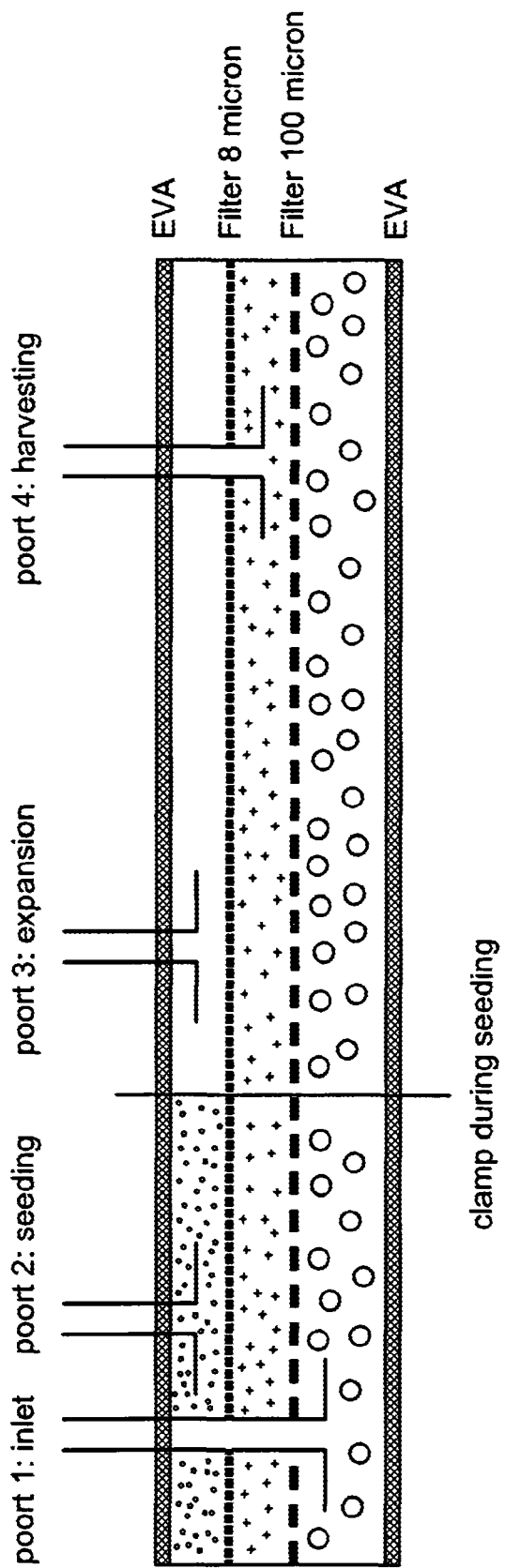
FIG. 2: schematic representation of use of the filters and portal in/outlets The present invention is directed to a method to expand adherent cells comprising
a) Addition of adherent cells to an expansion container comprising culture medium
b) Perfusing fresh medium through the expansion container and removing medium from the expansion container through 8-20 μm filter
c) Adding microcarriers
d) Allowing adherent cells to attach to microcarriers The method of the present invention comprises several steps to effectively expand adherent cells. Microcarriers are added to allow the adherent cells to attach. Adherent cells need a surface to grow on. Microcarriers are particles that have a high surface to volume ratio, to allow a large grow surface area for the adherent cells in a small volume. Microcarriers may be added either before the addition of the crude biopsy and/or medium but may be also added after the addition of the crude biopsy and/or medium. In a preferred embodiment, the microcarriers are added after the addition of the adherent cells and medium. After addition of the adherent cells, preferably fresh medium is passed through the expansion container while simultaneous medium is removed so that a constant volume and/or pressure are maintained. By removing medium from the expansion container through a filter with a pore size between 8 and 20 μm, blood cells and other small cells, are removed, and the adherent cells are retained in the expansion container. Preferred filters have a pore size of between 8 and 15 μm, more preferably between 8 and 12 μm, most preferably between 8 and 10 μm. The filtering through 8-20 μm filter may be performed before or after the adherent cells are allowed to attach to the microcarriers. In a preferred embodiment, first medium is removed by filtering through an 8-20 μm filter to remove blood cells and other small cells, before allowing the adherent cells to attach to the microcarriers. After a few days of culturing, other cells that did not pass through the filter, but also did not attach to the microcarriers may have died and have become smaller; these cells may then also be removed through the 8-20 μm filter. In a preferred embodiment, every medium that is removed from the expansion container is passed through an 8-20 μm filter. In order for the filter to work optimal, the filter preferably is non toxic for the adherent cells to be expanded. Furthermore it is beneficial if the adherent cells do not attach to the filter material.

The combination of microcarriers, a filter with pore size between 8-20 μm and a rocking regime of −30° to −90° to +30° to +90° and possibly a filter with a larger pore size between 50 and 100 μm, enable the use of crude biopsy for adherent cells to grow. Furthermore it was seen that it was beneficial to have smaller volume during the first seeding stage and a larger volume during the expansion stage. FIG. 2 shows a schematic representation of the use of the small and larger filter and the microcarriers in combination with the initial smaller volume with the later larger volume that may be used with the present invention.

Filter Material

For optimal application at least a small filter (+/−) 8-20 μm and possibly a larger filter (+/−) 50-100 μm filter may be integrated in a cell-culture-container. The filter material preferably does not allow cell attachment since cell attachment would block the filter during culture. Furthermore, the filter material is preferably not to be toxic for human mesenchymal stem cells (hMSCs). Therefore, the following filters have been tested on cell attachment and toxicity.

TABLE 7 filters tested on cell attachments and toxicity

| Product Nr. | Product number | Product name | Mesh opening (μm) | Material |
|---|---|---|---|---|
| 1 | 03-100/49 | SEFAR NITEX | 100 | Polyamide |
| 2 | 03-010/2 | SEFAR NITEX | 10 (8 not available) | Polyamide |
| 3 | 06-105/18 | SEFAR NITEX | 105 (100 not available) | Polyamide |
| 4 | 07-010/2 | SEFAR PETEX | 10 (8 not available) | Polyethylene-terephthalate/Polyester |
| 5 | 05-105/25 | SEFAR PROPYLTEX | 105 (100 not available) | Polypropylene |
| 6 | 07-11/5 | SEFAR MEDIFAB ® Polyester | 11 (8 not available) | Polyester |
| 7 | 07-100/32 | SEFAR MEDIFAB ® Polyester | 100 | Polyester |
| 8 | 03-15/10 | SEFAR MEDIFAB ® Polyamide | 15 (8 not available) | Polyamide |
| 9 | 03-60/42 | SEFAR MEDIFAB ® Polyamide | 60 (100 not available) | Polyamide |

The following conclusions have been drawn:

Based on visual inspection and cell counting it may be concluded that none of the tested filters are toxic for hMSC's.

Based on visual inspection it may be concluded that hMSC's do not attach to the tested filters but they prefer to attach to non tissue culture treated well plates instead to the tested filter materials.

The SEFAR MEDIFAB® product line enhance its ability to meet the strict manufacturing and cleanliness requirements of the medical industry. The SEFAR MEDIFAB® fabrics are composed of monofilament yarns, typically polyester (PET) and polyamide (PA). The raw materials (yarns) are produced in compliance with official regulations (e.g. 21CFR177). A separate validated processing line guarantees a high level of cleanliness and biocompatibility. In addition to the standard testing methods all SEFAR MEDIFAB® fabrics are routinely tested for endotoxins and hemolytic substances. USP class VI/ISO 10993 and cytotoxicity tests are performed at regular intervals and is therefore preferred for our application.

The best filtering results had been obtained by filter 03-15/10 "SEFAR MEDIFAB® Polyamide".

Based on visual inspection, cell counting and the Alamar Blue assay, may be concluded that Mesenchymal stem cells obtained from a human bone marrow biopsy prefer to attach to the Cytodex 1 microcarriers compared to filter 03-15/10.

Overall may be concluded that filter 03-15/10 "SEFAR MEDIFAB® Polyamide" is most suitable for our application. In addition, the 03-60/42 "SEFAR MEDIFAB® Polyamide" of 60 μm is preferred compared to a 100 μm filter since it had been noticed that Cytodex 1 microcarriers may break during culture, resulting in particles smaller than 100 μm.

In practice, the method and device of the invention allows the surgeon to inject a fresh biopsy, e.g. bone marrow aspirate of several cc in the closed bioreactor. The adult stem cells (mesenchymal stromal cells) are then culture expanded in a fully automated fashion so that days to weeks later the cells can be harvested and used for autologous (patient-own) or allogenous implantation to treat various tissue disorders varying from cardiovascular disease to bone defects.

The invention claimed is:

1. A method to expand adherent cells comprising
   a) adding adherent cells to an expansion container comprising culture medium;
   b) adding microcarriers;
   c) allowing cells to attach to microcarriers; and
   d) rocking the expansion container with movement at least between +30° and −30° from the horizontal position or rotating said container through +90° +0 −90° from the horizontal position, and
   wherein the expansion container has headspace of less than 10%.

2. The method according to claim 1 comprising an additional step
   e) perfusing fresh medium through the expansion container and removing medium from the expansion container through a filter.

3. The method of claim 2 wherein the filter has a pore size of 8-20 μm.

4. The method according to claim 1 wherein the adherent cells are present in a cellular biopsy.

5. The method according to claim 4 wherein the biopsy is taken from bone marrow, umbilicalcord blood, fat tissue, or peripheral blood.

6. The method according to claim 1 wherein the expansion container is disposable.

7. The method according to claim 1 wherein the volume of the expansion container is increased between 10 to 1500 ml.

8. The method according to claim 7 wherein the expansion container comprises a seeding volume and/or an expansion volume and wherein the seeding volume is between 10 to 400 ml, and the expansion volume is between 100 to 1500 ml.

9. The method of claim 7 wherein the volume of the expansion container is increased in a stepless manner.

10. The method according to claim 1 wherein the adherent cells, are selected from the group consisting of stem cells.

11. The method of claim 10 wherein the stem cells are mesenchymal stem cells.

12. The method according to claim 1 wherein the microcarriers provide a growth surface area from 100 to 60,000 $cm^2$.

13. The method according to claim 1 comprising an extra step wherein the adherent cells are detached from the microcarriers, and subsequently removed through a 50-100 μm filter.

14. The method of claim 1 wherein the headspace is absent.

15. The method of claim 1 wherein the rocking in d) is with movement between at least +50° and −50° from the horizontal position.

16. The method of claim 1 wherein the rocking in d) is with movement between at least +60° and −60° from the horizontal position.

17. The method of claim 1 wherein the rocking in d) is with movement between at least +80° and −80° from the horizontal position.

18. The method of claim 1 wherein the rocking in d) is with movement between at least +90° and −90° from the horizontal position.

* * * * *